United States Patent [19]

Raso

[11] Patent Number: 5,501,854
[45] Date of Patent: Mar. 26, 1996

[54] HYBRID REAGENTS CAPABLE OF SELECTIVELY RELEASING MOLECULES INTO CELLS

[75] Inventor: Victor A. Raso, Brookline, Mass.

[73] Assignee: Boston Biomedical Research Institute, Boston, Mass.

[21] Appl. No.: 998,754

[22] Filed: Dec. 28, 1992

Related U.S. Application Data

[63] Continuation of Ser. No. 482,001, Feb. 16, 1990, abandoned.

[51] Int. Cl.⁶ .............. A61K 39/395; A61K 39/40; C12P 21/08; C07K 16/46
[52] U.S. Cl. .............. 424/136.1; 424/143.1; 424/150.1; 424/178.1; 530/387.3; 530/388.2; 530/388.4; 530/391.1
[58] Field of Search .............. 530/391.1–391.9, 530/387.3, 388.4, 388.2; 424/85.8, 85.91, 136.1, 143.1; 435/188, 70, 21, 972

[56] References Cited

U.S. PATENT DOCUMENTS

| | | | |
|---|---|---|---|
| 4,470,925 | 9/1984 | Auditore-Hargreaves | 530/390 |
| 4,474,893 | 10/1984 | Reading | 436/547 |
| 4,479,895 | 10/1984 | Auditore-Hargreaves | 530/390 |
| 4,676,980 | 6/1987 | Segal et al. | 424/178.1 |
| 4,698,420 | 10/1987 | Urnovitz | 530/387.1 |

FOREIGN PATENT DOCUMENTS

| | | |
|---|---|---|
| 0068763 | 1/1983 | European Pat. Off. . |
| 0253202 | 1/1988 | European Pat. Off. . |
| WO83/03679 | 7/1983 | WIPO .............. G01N 33/54 |
| WO86/01409 | 5/1985 | WIPO . |
| WO87/01941 | 9/1986 | WIPO . |
| WO89/11867 | 5/1989 | WIPO . |
| WO89/11863 | 6/1989 | WIPO . |

OTHER PUBLICATIONS

Waldman Science vol. 252 1657 1991.
Hird *Genes and Cancer*; Corvey and Sikola ed. 1990.
Harris TibTech vol. 11, p. 42 1993.
Brennan et al (1985) Science 229:81–83.
Glennie et al (1981) J. Immunol 139(7):2367–2375.
Griffin et al (1987) Cancer Res. 47:4266–4270.
Alkan et al (1988) J. Interferon Res. 8(1):25–33 as represented by CA 108(3):110616m.
Laky et al (1987) Immunol. Lett. 14(2):127–32 See CA106 (23):188549v.
Moa et al (1988) Immunol. Lett 17(2):177–82 See CA108(13):106081v.
Schlossman et al (1988) GP 294703 Published 14 Dec. 1989 CA111CA):76400m.
Tsukada et al (1989) Cancer Biochem. Biophys. 10 (3):247–56.
Raso, V. and T. Griffin, *Cancer Res.*, 41:2073–2078 (1981).
Raso, V., *Immunological Rev.*, 62:93–117 (1982).
Raso & Basala, In: Receptor–Mediated Targeting of Drugs (1984).
Neville, et al., *Journal Biol. Chem.* 264(25):14653–14661 (1989) Medlini Abstract.
Paik et al., *The Journal of Nuclear Medicine* 30(10):1693–1701 (1989).

*Primary Examiner*—Lila Feisee
*Attorney, Agent, or Firm*—Hamilton, Brook, Smith & Reynolds

[57] ABSTRACT

Hybrid reagents comprising a first portion having an affinity for a cellular target and a second portion having an affinity for a bioactive molecule are described, said hybrid reagents being capable of selectively releasing the bioactive molecule in response to a change in pH. The hybrid reagents of the present invention can be used diagnostically or therapeutically.

6 Claims, 6 Drawing Sheets

HYBRID REAGENTS CAPABLE OF SELECTIVELY RELEASING MOLECULES INTO CELLS

GOVERNMENT FUNDING

The invention described herein was supported in whole or in part by the National Institutes of Health. The United States government has certain rights to this invention.

This is a continuation of application Ser. No. 07/482,001 filed on Feb. 16, 1990, now abandoned.

BACKGROUND OF THE INVENTION

Hybrid antibodies are antibodies or aggregates of antibodies which are specific for two different antigens. Hybrid antibodies can comprise a single antibody or fragment having a bispecific antigen binding region (two different variable regions) or aggregates of two or more antibodies of different specificities.

Different methods of preparing hybrid antibodies have been reported. Auditore-Hargreaves teaches processes for preparing hybrid antibodies by generating "half molecules" from two parent antibodies and subsequently associating different half molecules. See U.S. Pat. Nos. 4,470,925 (1984) and 4,479,895 (1984). Using this process, various hybrid antibodies were prepared with specificities for horseradish peroxidase, glucose oxidase and theophylline.

Reading describes production of antibodies having binding specificities for two desired antigens using a quadroma cell or a trioma cell. See U.S. Pat. No. 4,474,893 (1984). The quadroma cell is the fusion product of two different hybridoma cells, each of which produce an antibody with a different specificity. A trioma cell is the fusion product of a hybridoma and a lymphocyte which produces antibodies with two different binding specificities.

Segal et al. describe target specific crosslinked heteroantibodies which are used as cytotoxic agents in U.S. Pat. No. 4,676,980 (1987). Staerz et al. (1986), *PNAS*, 83:1453–1457, teach the use of a hybrid antibody that can focus effective T cell activity and Milstein et al. (1983), *Nature*, 305:537–539, describe the use of hybrid antibodies in immunohistochemistry.

Raso et al., *Cancer Research*, 41:2073–2078 (1981) disclose the use of hybrid antibodies with dual specificity for the plant toxin, ricin, and immunoglobulin-bearing target cells. The hybrid antibodies were constructed in vitro and the attachment of the hybrid antibody-ricin complex to the human target cells was observed using fluorescein labeled antibodies. Upon binding, the human target cells were selectively killed by the hybrid-delivered toxin.

Prior to the use of hybrid antibodies, chemical crosslinking or nonspecific absorption methods were used to couple drugs and/or toxins to antibody carriers. These agents possess certain limitations due to the nature of the linkage. The linkage may alter the drug or toxin such that the therapeutic or toxic activity is reduced. Moreover, cleavage of the covalent bond may be rate-limiting for the action of toxin inside the cell.

The use of hybrid antibodies obviated some of the problems encountered with chemical crosslinking or non-specific absorption methods; however, new problems were created. Because the drug or toxin is bound to an antibody, the therapeutic or toxic activity is generally inhibited. Hybrid antibody-delivered toxins or drugs are inactive when bound to the antibody and only become active upon release. However, the hybrid antibodies currently available have no mechanism for releasing the toxin or drug from the respective antibody binding region when the hybrid antibody reaches the target site or the interior of the cell. Instead, they rely on fortuitous dissociation. As a result, relatively large quantities of hybrid antibodies containing drugs or toxins must be administered, because only a small amount of the drug or toxin will dissociate and become active.

SUMMARY OF THE INVENTION

This invention pertains to hybrid reagents comprising a first portion having an affinity for a cellular target (e.g., antibody, virus, ligand, receptor or molecule) and a second portion having an affinity for a bioactive molecule (e.g., a toxin, drug, enzyme or metal). The hybrid reagents can be administered in vivo where they bind to the external surface of a cell. Once bound to the cell, receptor-mediated endocytosis serves to pinch off the surface of the cell forming an endosome, which has a lower pH than either outside or within the rest of the cell. In response to the pH change inside the endosome, the hybrid reagents of the present invention selectively release the bioactive molecule. Once released, the bioactive molecule is free to perform its function.

Therefore, a major advantage of hybrid reagents of this invention over currently available hybrid antibodies, which rely on fortuitous dissociation of bioactive molecules, is that less of the hybrid and bioactive molecule need to be administered to produce the desired diagnostic or therapeutic effect.

The present invention also encompasses pharmaceutical compositions comprising said hybrid reagents having a bioactive molecule bound thereto, methods of immunotherapy and a method for selecting antibodies or fragments thereof capable of binding a bioactive molecule at one pH and releasing that molecule in response to a change in pH.

DETAILED DESCRIPTION OF THE INVENTION

The hybrid reagents of this invention comprise a first portion having an affinity for a cellular target and a second portion having an affinity for a bioactive molecule (e.g., a toxin, drug, metal or an enzyme). The hybrid reagents can be administered in vivo where they bind to the external surface of a cell. Once bound to the cell, receptor-mediated endocytosis serves to pinch off the surface of the cell forming an endosome, which has a lower pH than either outside or within the rest of the cell. In response to the change in pH within the endosome, the hybrid reagents selectively release the bioactive molecule. The first portion of the hybrid can be, for example, a ligand (e.g., transport proteins such as transferrin, interleukin-2, LDL), a growth factor (e.g., EGF, PDGF), an antibody, a hormone, a receptor molecule (e.g., recombinant CD4), a virus, or a fragment thereof and the second portion is an antibody or an antibody fragment.

The first portion of the hybrid reagent has an affinity for a cellular target, such as an antigenic or receptor site on the surface or inside a cell (i.e., a cell surface antigen or cell surface receptor). Examples of cellular targets are Ig, common acute lymphoblastic leukemia antigen (CALLA), B1, gp26, Ia, transferrin receptor, EBV transformation antigen and the receptors for ligands such as interleukin-2, MSH, insulin, thyroglobulin, LHRH and NGF. Viral proteins on the surface of infected cells (e.g., HIV-infected T-lymphocyte) can also serve as targets for antibody and receptor guided hybrid reagents.

The second portion of the hybrid reagent is an antibody or antibody fragment that has an affinity for a bioactive molecule at one pH and releases the bioactive molecule in response to a change in pH. This bonding and release may be due to a number of mechanisms. For example, the second portion of the hybrid reagent may have an affinity for a bioactive molecule that undergoes a conformational change in response to a change in pH. Such molecules can be identified by using physical or other methods known in the art (e.g., circular dichroism, fluorescence). As another example, the second portion of the hybrid reagent may ionically bond to a bioactive molecule at one pH and the ionic bond may break in response to a change in pH.

A method for isolating antibodies that dissociate from molecules in response to a change in pH is described in detail in Example 1. In general, antibodies against a bioactive molecule are prepared using known techniques. Clone supernatants are then assayed for the ability to bind the molecule at the first selected pH. Clones testing positive for binding ability are screened to isolate those that release the molecule at a second selected pH. For example, antibodies that bind a bioactive molecule at physiologic pH (pH about 6.5 to 7.5) can be tested to isolate those clones that release the molecules at acidic pH (pH less than 6.5).

Examples of bioactive molecules are plant or bacterial toxins, drugs, enzymes and metals. Examples of useful toxins are diphtheria toxin, pseudomonas exotoxin, ricin, pokeweed antiviral peptide (PAP), and tricathecum. The toxins can also be genetically or chemically altered or mutated such as CRM107 (Laird *J. Virol.*, 19:220–227 (1976)) and HA48DT and HA51DT (Myers et al., *J. Biol. Chem.*, 263:17122–17127 (1988)). Drugs which can be used in the invention are for example, interferon, insulin, and methotrexate. Examples of metals which can be used in the invention are radiometals (e.g., Tc-99m, In-111, Cu-67, Pd-109, Pd-103, Re-188, Au-198, Au-199, Ru-97, Hg-197, Ag-111, Bi-212, Os-191 and Pb-203) and non-radioactive metals (e.g., zinc).

Figure 1:
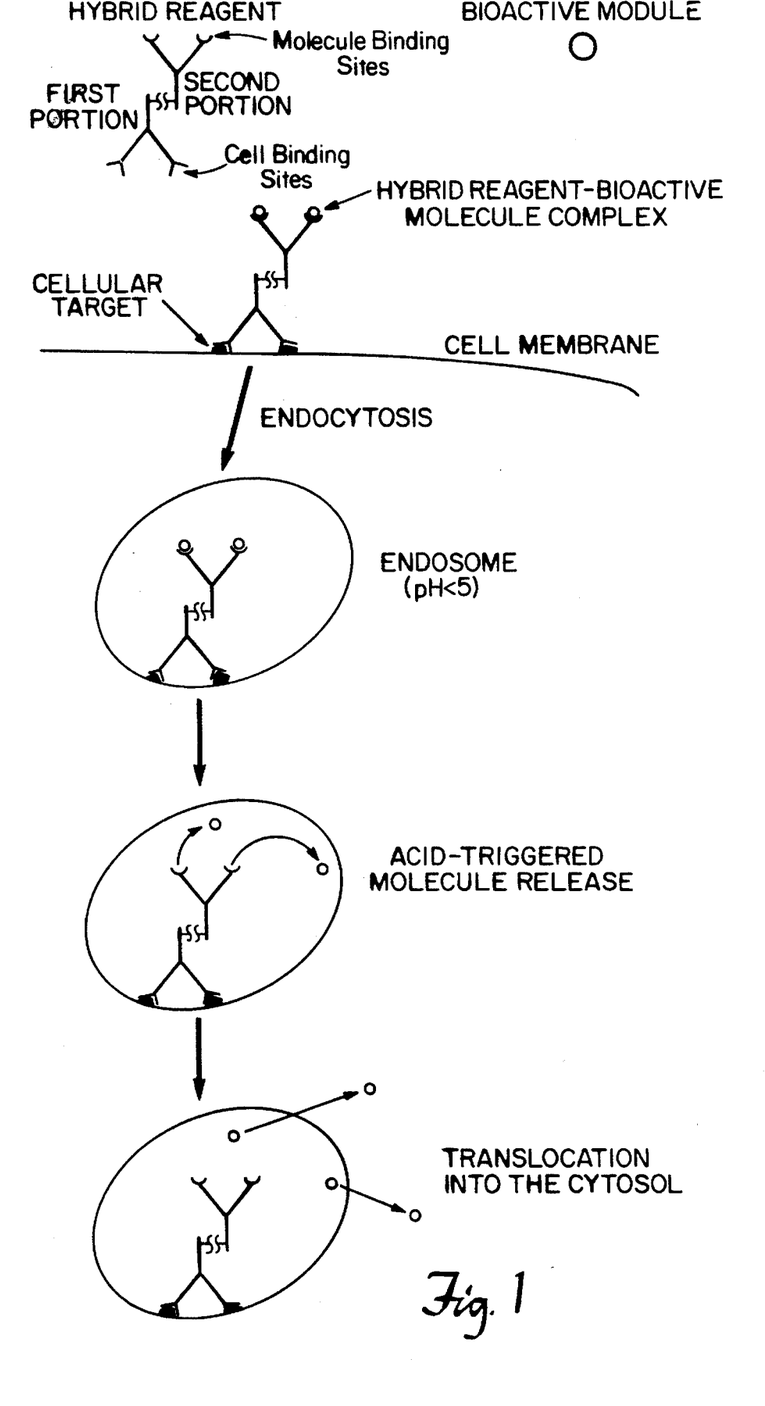
FIG. 1 is a schematic diagram depicting the delivery to a cell of a bioactive molecule from a hybrid reagent by receptor mediated endocytosis and release of the bioactive molecule in response to the lower pH found within a cellular endosome.
Figure 2:
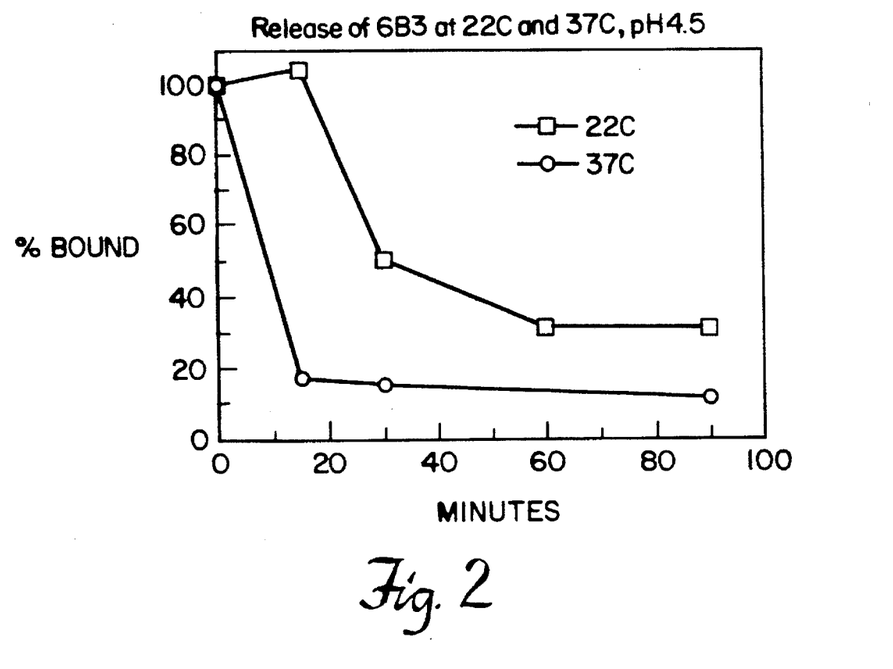
FIG. 2 is a graph plotting the percent dissociation (i.e., release) of monoclonal antibody 6B3 from diptheria toxin over 100 minutes time at a pH of 4.5 and temperatures of 22° C. and 37° C.
Figure 3:
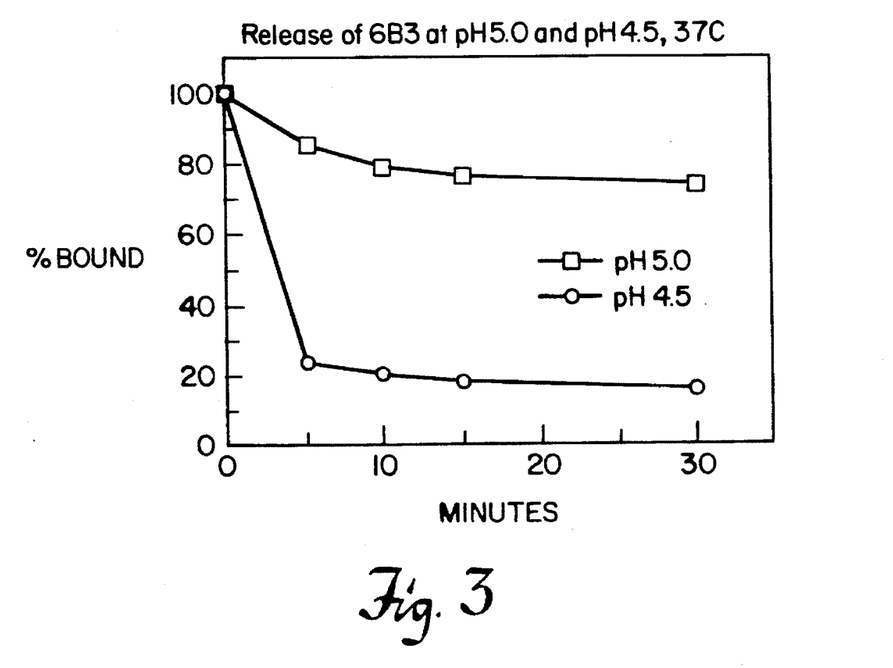
FIG. 3 is a graph plotting the percent dissociation of monoclonal antibody 6B3 from diptheria toxin over 30 minutes time at pH 5.0 and pH 4.5 at 37° C.
Figure 4:
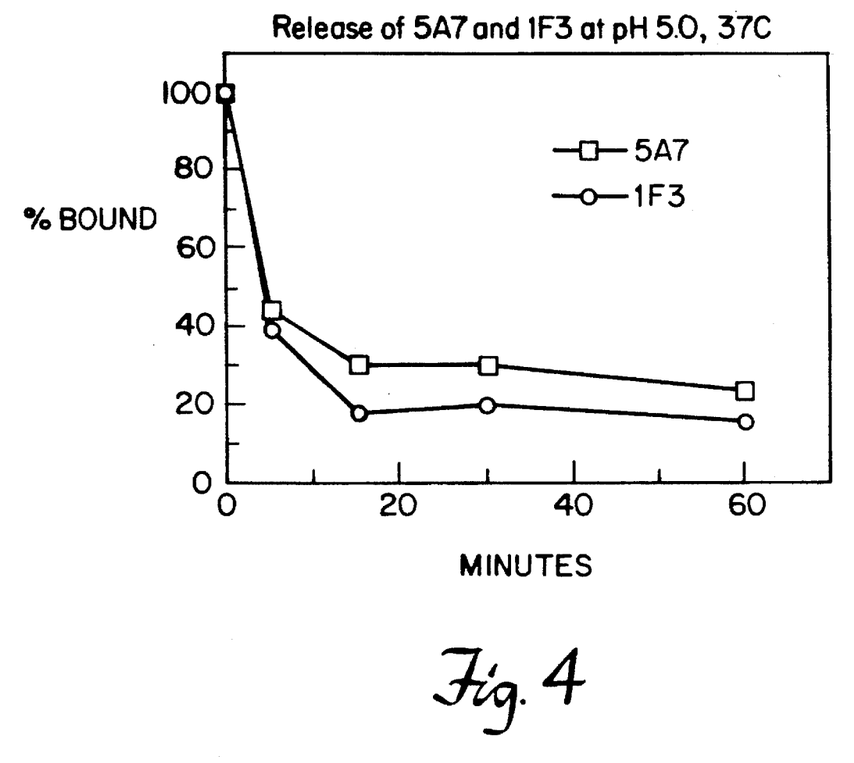
FIG. 4 is a graph plotting the percent dissociation of monoclonal antibodies 5A7 and 1F3 from diphtheria toxin over 60 minutes time at pH 5.0 at 37° C.

FIG. 1 illustrates receptor-mediated endocytosis of a hybrid reagent-molecule complex. The first portion of the hybrid reagent binds to the external surface of the cell, which becomes pinched off to form an endosome. Endosomes have a pH lower than (e.g., pH about 4.5–5.5) the pH either outside or within the rest of the cell (e.g., pH about 6.5–7.5) (Geisow, M. L. and W. H. Evans, *Exp. Cell Res.*, 150:36–46 (1984)). Therefore, by using a hybrid reagent in which the first portion has an affinity for a cell surface component and the second portion has an affinity for a bioactive molecule at physiologic pH and dissociates from the bioactive molecule in response to acidic pH, a molecule can be delivered into a cell and released within acidic compartments of cells, such as cell endosomes.

The hybrid reagents can be produced by joining together the first and second portions using known techniques (e.g., chemical coupling, cell fusion, or genetic engineering techniques). The hybrid reagents are preferably made by chemically coupling the two portions together. For example, a disulfide linkage using N-succinimidyl-3-(2-pyridyldithio) propionate (SPDP) as the crosslinking agent can be used (Raso et al., *NATO Advanced Studies Institute*, 82:119–138 (1984)). Both portions become sparingly substituted with pyridyldisulfide groups which are reduced to thiols on one of the portions. Upon mixing of the two portions, the free thiols on one of the portions readily reacts with the unreduced groups on the second portion and form disulfide linkages. The resulting hybrids can then be purified using gel filtration.

When the first and second portions of the hybrid reagent are both antibodies, two whole parental antibodies may be joined together to produce the hybrid reagent (i.e., hybrid antibody). A variety of crosslinking agents, such as protein A, carbodiimide, and N-succinimidyl-3-(2-pyridyldithio) propionate (SPDP) can be used to link the whole parental antibodies (Kranz et al., *Proc. Natl. Acad. Sci. USA*, 78:5807 (1981).

The hybrid antibodies can also be produced by chemically joining parental antibody fragments containing a sufficient portion of the antigen binding region to allow the fragment to bind to its respective antigen (Nisonoff et al., *Arch. Biochem. Biophys.*, 93:460–467 (1961) and Raso et al., *Cancer Research*, 41:2073–2078 (1981)). The two types of parental antibodies (i.e., one type will become the first portion of the hybrid antibody and the other type will become the second portion) can then be separately digested with pepsin. Bivalent F(ab')$_2$ molecules are obtained after a separation step such as chromatography. Equal amounts of the 2F(ab')$_2$ types can then be mixed and after reducing their inter-heavy chain disulfide linkages, the resulting Fab' fragments are allowed to randomly reassemble into F(ab')$_2$ dimers with dual specificity. The dual specificities of the hybrid product can be verified using cell-based and solid phase assays which use radioactive or fluorescent probes (Raso, V., *Immunol. Reviews*, 62:93–117 (1982)).

Alternatively, the intrinsic disulfide links of the F(ab')$_2$ molecules can be reduced to thiols and the vicinal thiols generated can be stabilized (e.g., with sodium arsenite). Ellman's reagent can be used to activate the vicinal thiols on one type of the Fab' fragments. Upon mixture of the reduced Fab' fragment with an activated Fab' fragment, an exclusively bi-specific hybrid will be formed (Brennan, M., et al., *Science*, 228:81–83 (1985)).

The hybrid antibodies can also be produced using cell fusion techniques as described in U.S. Pat. No. 4,474,893, to Reading. In this technique, hybridoma cells which secrete the parental antibodies are fused together to form quadroma or trioma cells. These quadroma and trioma cells secrete bi-specific antibodies possessing the antigen binding regions of both parental antibodies.

In addition, the hybrid antibodies can be produced using genetic engineering techniques. In these procedures, DNA encoding the heavy and light chain variable regions of each of the parental antibodies are introduced into an appropriate host cell, preferably a lymphoid cell (e.g., a myeloma cell). The transformed cell can then synthesize, assemble and secrete the hybrid antibody.

The parental antibodies used to produce the hybrid antibody can be selected from those presently available or can be specially prepared. The parental antibodies can be obtained using conventional monoclonal antibody methodology, (e.g., the standard somatic cell hybridization techniques of Kohler and Milstein, *Nature*, 256:495 (1975)).

Suitable antibodies which are specific towards tumor associated antigens and are therefore appropriate to comprise the first portion of the hybrid reagent, are for example, 7D3, directed against the human transferrin receptor, (Griffin et al., *Cancer Res.*, 47:4266 (1987)); C19, directed against the carcinoembryonic antigen, (Griffin et al., *J. Biol Resp. Modif.*, 1:194 (1982)); 260F9, directed against a breast cancer antigen, (Bjorn et al., *Cancer Res.*, 45:1214 (1985)); 96.5 directed against a melanoma associated antigen, (Casellas et al., *In. J. Cancer,* 30:437 (1982)); 45-2D9, directed against an oncogene product, (Roth et al., *J. Immunol.*, 136:2305 (1986)) and J-5, directed against the common acute lyphoblastic leukemia antigen, (Raso et al., *Cancer Res.*, 42:457 (1982)).

Suitable antibodies which are specific towards diptheria toxin and are capable of releasing the toxin in response to a change in pH from physiologic to acidic, are D5E8, D1F3, D3E1, D6B3, D5D5, D1D5, D5F5 and D4B7. These antibodies are therefore appropriate to comprise the second portion of the hybrid reagent.

The hybrid reagents described herein can be used diagnostically. For example, hybrid molecules comprising a first portion which has an affinity for a tumor cell and a second portion which has an affinity for a radiometal can be used to deposit radiometal within tumor cells and thereby obtain a scintographic image of the tumor.

Hybrid reagents of this invention can also be used therapeutically. For example, hybrid molecules comprising a first portion having an affinity for a viral-associated antigen (e.g., an HIV antigen) or a viral-associated receptor and a second portion having an affinity for a bioactive molecule, can be used therapeutically to kill or otherwise modify virus infected cells. Similarly, hybrid molecules comprising a first portion having an affinity for a tumor-associated antigen or a tumor-associated receptor and a second portion having an affinity for a bioactive molecule can be used therapeutically to kill or otherwise modify tumor cells.

When the hybrid reagent described herein is used in a pharmaceutical composition, it can be administered by a wide variety of techniques. For example, intravenously, parenterally, transdermally subcutaneously or via an implanted reservoir containing the hybrid molecule. The form in which the hybrid molecule will be administered (e.g., solution, emulsion) will depend on the route by which it is administered. The quantity of the hybrid molecule to be administered will be determined on an individual basis and will be based at least in part on consideration of the individual's size, the severity of the symptoms to be treated, and the result sought.

This invention is further illustrated by the following examples.

EXAMPLE 1

The Isolation of Anti-Diphtheria Toxin Antibodies Capable of Releasing a Molecule at a Selected pH Mice were immunized with progressively increasing doses of active diphtheria toxin (1 μg–3 μg I.P.) or a high dose of formalin-inactivated diphtheria toxoid (100 μg I.P.). Following a booster injection of the immunogen, spleens were removed and fused with NS-1 cells to generate hybridomas (Kohler and Milstein, *Nature,* 256:495 (1975)). Supernatants from microtiter wells with clones were assayed for the ability to bind $^{125}$I-diphtheria toxin using a polyethylene glycol precipitation method. Antibody positive supernatants usually bound 25,000 cpm while negatives and controls bound only 4,000 cpm. In a typical fusion approximately 35 positive clones were obtained from the spleen of a single animal.

A second assay was developed in order to examine the influence of pH on the interaction between diphtheria toxin and the different monoclonal antibodies. Diphtheria toxin (100 μl at 300 μg/ml) was absorbed to polyvinyl microtiter wells, excell was washed off with PBS. Antibody (100 μl at 1–50 μg/ml) was then added, allowed to react for two hours and the plate was washed with PBS. Attached antibody was revealed by subsequent addition of a $^{125}$I-goat antimouse IgG reagent (background was approximately 100 cpm, positive clones bound approximately 1,000–3,000 cpm).

To test for pH effects on toxin release, the antibody was allowed to bind to the immobilized diphtheria toxin for two hours in replicate wells and then a small volume of concentrated buffer was added to provide a final pH of 7.0, 5.0 or 4.5. Dissociation was allowed to proceed for different time intervals (5–90 minutes) at either 23° C. or 37° C. (normal body temperature). Released antibody was quickly washed off the plates with PBS and the amount remaining was quantified using a $^{125}$I-goat antimouse IgG probe. This method was used to identify 23 clones producing antibody which rapidly dissociated from diphtheria toxin at a pH of 4.5 and eight clones having antibody that was sensitive to release at a pH of 5.0. No release occurred at a pH of 7.0.

The time-course of dissociation at pH 4.5 for one of these monoclonal antibodies (D6B3) is shown in FIG. 2. At 23° C. the rate of release was slower and less complete than at 37° C. Approximately 80 percent of the antibody initially bound dissociated from diphtheria toxin and most of this occurred within the first 5 minutes. It is known that the diphtheria toxin remains attached to the assay plate since binding of monoclonal antibodies derived from different clones remained completely unaffected by the same acid conditions.

FIG. 3 shows that the binding interaction of this D6B3 antibody was much less sensitive to release at pH 5.0, with only 25 percent having dissociated by 30 minutes in contrast to 80 percent at pH 4.5 The kinetics of release for two monoclonal antibodies which did dissociate at pH 5.0, at 37° C. is shown in FIG. 4. The binding interaction between D5A7 and diphtheria toxin was even disrupted at pH levels as high as 5.5. Thus a substantial fraction of diphtheria toxin was rapidly relinquished by these different antibodies at the precise pH and temperature conditions found in endosomal vesicles and other acidic compartments within cells (Geisow, J. L. and W. H. Evans, *Exp. Cell Res.*, 150:36–46 (1984)).

The pH-dependent break-up of antibody and toxin was shown to be based upon conformational changes in the toxin. Thus, the $t_{1/2}=1-2$ min for the acid triggered dissociation of antibody and toxin is close to the $t_{1/2}=30$ sec for the pH-induced transition of free toxin (Blewitt, M. G., et al., *Biochem.*, 24:5458–5464 (1985)). Moreover, the D6B3 antibody bound to formalin stabilized diphtheria toxoid at pH 7.0 but did not release when the pH was reduced to pH 4.5. Apparently the chemical crosslinking of toxoid prevented the pH-induced transition which allows D6B3 to dissociate from native toxin.

EXAMPLE 2

Hybrid-Mediated Delivery of $^{125}$I-Diphtheria Toxin to Cells

Hybrid antibodies were formed with various anti-diphtheria toxin antibodies by linking them to anti-transferrin receptor monoclonal antibodies by a method previously described (Raso, F., et al., *NATO Advanced Studies Institute*, 82:119–138 (1984)). The dual specificity and cell targeting capability of these hybrids was demonstrated using $^{125}$I-diphtheria toxin (hereinafter $^{125}$I-DT). CEM cells derived from a patient with T-cell leukemia (Foley, G. E., et al., *Cancer*, 18:522–529 (1965)), which have abundant transferrin receptor on their surface, were used as a test line for anti-transferrin receptor/anti-diphtheria toxin hybrids and two different routes of delivery were tested. The cells were either pre-treated with the hybrid and washed so that the empty toxin binding sites of surface-bound hybrids could then capture subsequently added $^{125}$I-DT; or hybrid plus $^{125}$I-DT were pre-complexed and then used as a single agent for reaction with the cell surface transferrin receptors.

CEM cells were incubated with the components designated in Table I for 30 minutes at 0° and then washed with PBS to remove unbound hybrid. They were then exposed to $^{125}$I-DT for 30 minutes at 0°, washed with PBS and counted to measure the amount bound to cells.

The results in Table I show that cells exposed to an anti-transferrin receptor/anti-diphtheria toxin hybrid (7D3/D1F3) bound five times higher levels of $^{125}$I-DT than untreated cells. This enhanced binding was receptor-specific since preoccupying the target epitope using excess unmodified 7D3 antibody blocked hybrid attachment and subsequent $^{125}$I-DT binding (Table I). Hybrids formed with different anti-diphtheria toxin monoclonal antibodies (D4B7 and D5E8) showed similar toxin binding properties (Table I).

TABLE I

Binding of $^{125}$I-DT to Hybrid-Coated CEM Cells

| Pretreatment | CPM Bound |
| --- | --- |
| None | 888 |
| 7D3/D1F3 Hybrid | 4,381 |
| Excess 7D3 plus 7D3/D1F3 Hybrid | 973 |
| None | 556 |
| 7D3/D4B7 Hybrid | 4,306 |
| 7D3/D5E8 Hybrid | 5,657 |

CEM cells were treated for 1 hour at 0° C. with an equivalent amount of $^{125}$I-DT either alone in PBS or pre-complexed at 22° for 15' to hybrid at $10^{-8}$M (Table II).

Following treatment, the cells were washed with PBS and counted. Table II shows that significant delivery over the basal binding levels was attained even though the concentration of complex used to treat these cells was relatively low ($10^{-8}$M).

TABLE II

Delivery of Hybrid-Complexed $^{125}$I-DT to CEM Cells

| Treatment | CPM Bound |
| --- | --- |
| $^{125}$I-DT alone | 1,649 |
| 7D3/D4B7 Hybrid - $^{125}$I-DT complex | 13,116 |
| 7D3/D5E8 Hybrid - $^{125}$I-DT complex | 15,297 |

EXAMPLE 3

Plate Assay for Dual Specificity of HIV-Directed Hybrids

An anti-HIV monoclonal antibody was elicited using a synthetic envelope protein and used to form the HIV-specific hybrid (anti-HIV/D5E8) by coupling it to an anti-diphtheria toxin antibody (D5E8) following a method previously described (Raso, F., et al., *NATO Advanced Studies Institute*, 82:119–138 (1984)). A solid-phase radioimmunoassay was devised by adsorbing the envelope peptide antigen to the wells of polyvinyl microtitre plates. PBS and either antibody or hybrid at $6 \times 10^{-9}$M was then added to the well for 2 hrs, and any unbound reagent was washed off using PBS. The dual specificity of the hybrid was demonstrated after allowing it to bind to the coated plate via its HIV-specific combining sites and then revealing its presence by binding $^{125}$I-CRM107 to the free toxin-specific sites of the composite molecule. Table III shows that the anti-HIV/D5E8 hybrid bound $^{125}$I-CRM107 while anti-HIV alone bound no toxin even though it was attached to the plate as evidenced by using an $^{125}$I-goat anti-mouse IgG probe.

TABLE III

Plate Assay to Demonstrate the Binding of Anti-HIV Antibody and Hybrid

| | Amount Bound (CPM) | |
| --- | --- | --- |
| | $^{125}$I-CRM107 | $^{125}$I-G/M |
| PBS | 307 | 253 |
| anti-HIV | 112 | 1,501 |
| anti-HIV/D5E8 Hybrid | 1,245 | — |

EXAMPLE 4

Hybrid-Mediated Cytotoxicity of a Mutated Form of Diphtheria Toxin

The availability of genetically or chemically altered diphtheria toxin cogeners (e.g., CRM107) with no capacity for attaching to cells provides an added dimension to the hybrid delivery approach. The cell-binding defect which makes these analogs non-toxic to cells can be restored via the hybrid carrier moiety so that its lethal action is aimed exclusively at the selected cell surface target.

Human mesothelioma cells (H-Meso) were used to test the effectiveness of anti-transferrin receptor/anti-diphtheria toxin hybrids (7D3/D1F3 and 7D3/D5E8) for restoring the full cytotoxic potential of CRM107. The H-meso cells were incubated for 2 hours at 37° C. with $4\times10^{-8}$M CRM107 alone; $(4\times10^{-8}$M) CRM107 in combination with the hybrids 7D3/D5E8 or 7D3/D1F3 at $1\times10^{-8}$M, or $4\times10^{-8}$M CRM107 in combination with the hybrids $(1\times10^{-8}$M) plus excess anti-receptor antibody (7D3) $(10^{-5}$M). Cells were then pulse labeled with $^3$H-leucine for 30 min. H-meso cells in media to which 10 mM NH$_4$Cl was added were also incubated with the same components.

The data in Table IV show that while CRM107 alone was incapable of entering cells and inhibiting protein synthesis, it became a very potent and rapid-acting cytotoxin when used in combination with the hybrid antibodies. This lethal action was dependent upon hybrid-mediated delivery to transferrin receptors since little toxicity was obtained when these sites were blocked by including an excess of free anti-receptor antibody (7D3) during the 2 hour incubation time (Table IV).

The acid environment of intracellular compartments is essential for cytotoxicity since this induces the release of CRM107 from the antibody and translocation into the cytosol where it inactivates elongation factor 2. This condition was demonstrated by adding NH$_4$Cl to the cells. This weak base, which is known to raise vesicle pH, greatly reduced the ability of the hybrid-CRM107 combination to kill H-Meso cells (Table IV). The same experiments were carried out using the anti-HIV/D5E8 hybrid $(2\times10^{-8}$M) plus CRM107 $(4\times10^{-8}$M) using HIV-infected 8E5 cells as the target (Folks, T. M., et al., *J. Exp. Med.*, 164:280–290 (1986)). The same acid-dependency was demonstrated (Table V).

TABLE IV

Hybrid-Mediated Cytotoxicity of CRM107 Tested on Human Mesothelioma Cells (2-hr Assay); Transferrin Receptor Specificity and Acid-Dependency

|  | $^3$H-Leucine Incorporation (CPM) | Inhibition (Percent) |
|---|---|---|
| H-Meso Cells | 92,560 | — |
| +CRM107 | 90,755 | 2 |
| +7D3/D5EB + CRM107 | 1,605 | 98 |
| +7D3/D1F3 + CRM107 | 8,050 | 91 |
| +excess 7D3 + 7D3/D5E8 + CRM107 | 52,325 | 43 |
| +excess 7D3 + 7D3/D1F3 + CRM107 | 53,960 | 42 |
| H-Meso Cells + 10 mM NH$_4$Cl | 92,435 | — |
| +CRM107 | 76,885 | 17 |
| +7D3/D5E8 + CRM107 | 52,105 | 44 |
| +7D3/D1F3 + CRM107 | 80,802 | 13 |

TABLE V

Acid-Dependency of Hybrid-Mediated Cytotoxicity of CRM107 on HIV-Positive 8E5 Cells

|  | $^3$H-Leucine Incorporation (CPM) | Inhibition (percent) |
|---|---|---|
| HIV-Positive + 8E5 cells alone | 103,955 | — |
| +CRM107 | 85,140 | 18 |
| +NH$_4$Cl + CRM107 | 82,115 | 21 |
| +anti-HIV/D5E8 + CRM107 | 21,820 | 79 |
| +NH$_4$Cl + anti-HIV/D5E8 + CRM107 | 78,985 | 24 |

The transferrin receptor directed hybrid-CRM 107 complex was assayed on human colon adenocarcinoma cells to determine if the same high cytotoxic potency found for the H-Meso and HIV-infected 8E5 cell lines extended to alternative malignant cell types. The combined action of CRM107 plus hybrid at $10^{-8}$M produced extensive cell kill within two hours and its potency was comparable to $10^{-7}$M native diphtheria toxin (Table VI). These results indicate that hybrid-delivery not only renders CRM107 cytotoxic to cells but also suggests that its entry via the transferrin pathway is as efficient as diphtheria toxin uptake by its usual mechanism. Moreover, a transferrin/D5E8 conjugate was constructed to examine if transferrin itself would mediate delivery of CRM107 into cells. In fact, this natural ligand coupled to the anti-diphtheria toxin monoclonal antibody (D5E8) provided a similar level of toxicity as the anti-transferrin receptor (7D3) guided hybrid.

TABLE VI

Lethal Effects of Anti-Transferrin Receptor Directed Hybrid Plus CRM107 on Human Colon Adenocarcinoma Cells (2-hr. Assay)

|  | $^3$H-Leucine Incorporation (CPM) | Inhibition (Percent) |
|---|---|---|
| LS174T cells | 54,070 | — |
| +CRM107 $(10^{-7}$M) | 48,355 | 11 |
| +7D3/D5E8 $(10^{-8}$M) + CRM107 $(10^{-7}$M) | 1,930 | 96 |
| +Diphtheria Toxin $(10^{-7}$M) | 1,785 | 97 |
| +Diphtheria Toxin $(10^{-8}$M) | 6,295 | 88 |

In addition to using the transferrin receptor as a target for hybrid delivery, the common acute lymphoblastic leukemia antigen (CALLA) was similarly tested as a site of entry into CALLA-bearing Nalm-1 leukemia cells (Raso, V., et al., *Cancer Res.*, 42:457–464 (1982)). An anti-CALLA/D5E8 hybrid was formed and examined for its ability to kill these cells in combination with CRM107 following the protocol set forth for H-meso cells and anti-transferrin receptor/anti-diphtheria toxin. However, incubation was carried out for 6 hours at the same temperature (Table VII).

Good cell kill was achieved by targeting the hybrid-CRM107 to this distinct membrane site; however, the longer incubation time required suggests that entry and/or release of toxin was slower than for transferrin receptor directed agents.

TABLE VII

CALLA-Directed Cytotoxic Action of Hybrid-CRM107 on Nalm 1 Cells (6-hr. Assay)

|  | $^3$H-Leucine Incorporation (CPM) | Inhibition (Percent) |
|---|---|---|
| Nalm-1 Cells | 22,130 | — |
| + anti-CALLA/D5E8 | 24,110 | 0 |
| + CRM107 | 22,820 | 0 |
| + anti-CALLA/D5E8 + CRM107 | 4,080 | 82 |

EXAMPLE 5

Kinetics of Cytotoxicity in H-Meso Cells

One of the fundamental premises underlying the acid-triggered hybrid carrier concept predicts that this mode of delivery will not interfere with the normal mechanism of toxin action after specific targeting has been achieved. A critical measure of toxin efficiency can be obtained by monitoring the kinetics of inhibition of protein synthesis.

Figure 5:
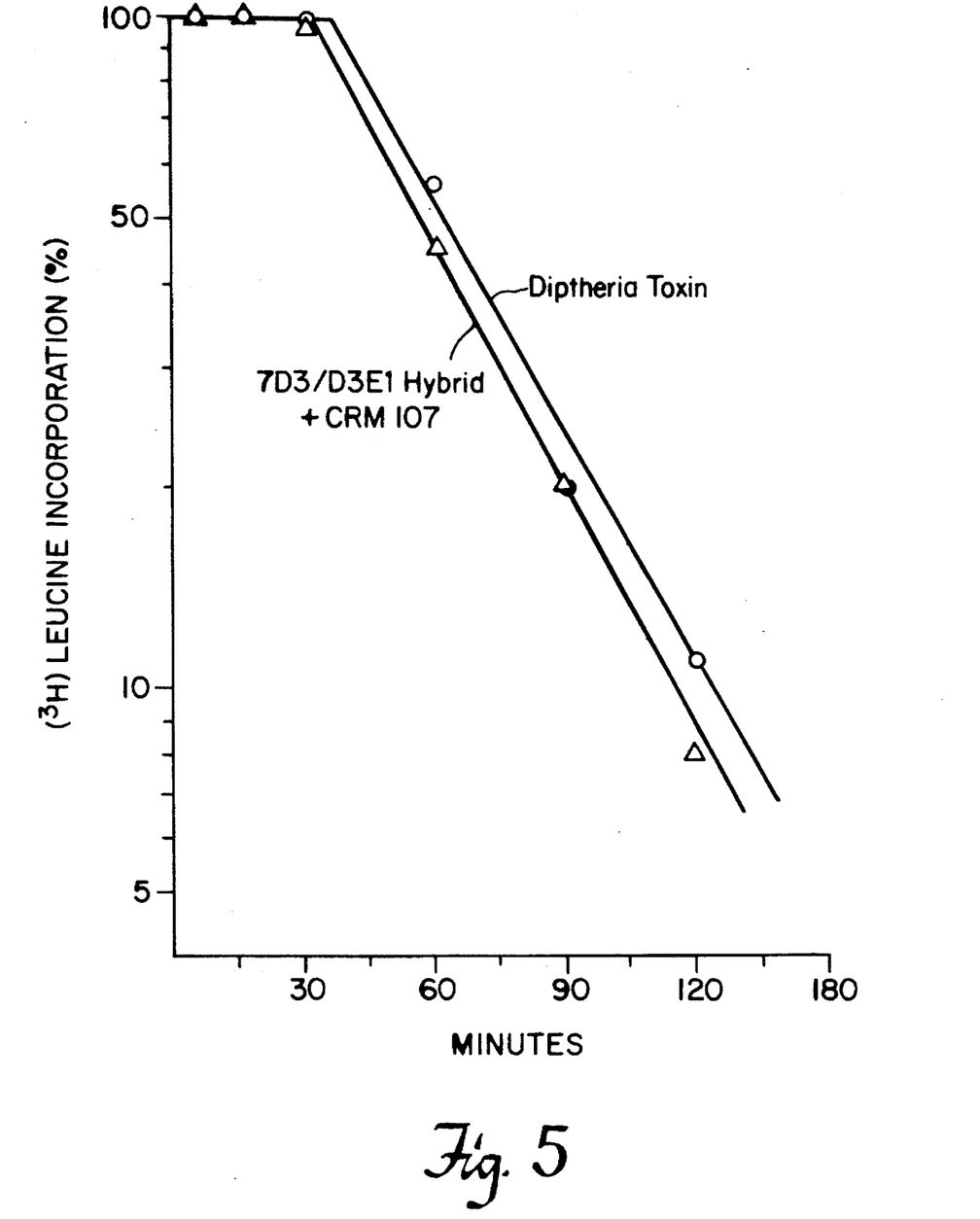
FIG. 5 is a graph plotting the percent incorporation of $^3$H leucine over 180 minutes time as a measure of protein synthesis inactivation by native diphtheria toxin and hybrid-delivered CRM107 in H-meso cells.

This parameter accurately indicates how rapidly toxin gains access to its target in the cytosol (e.g., elongation factor 2) and was therefore used to evaluate hybrid-delivered CRM107 (FIG. 5).

H-Meso cells were incubated at 37° C. for the designated intervals with either $10^{-8}$M diphtheria toxin, $10^{-8}$M CRM107, or the anti-transferrin receptor/anti-diphtheria toxin hybrid (7D3/D3E1)-CRM107 combination at $10^{-8}$M. The cells were then pulse labeled with $^3$H-leucine for 30 minutes to measure the extent incorporation into protein compared to untreated control cells. The time course of protein synthesis inhibition as reflected by $^3$H-leucine incorporation, for H-Meso cells incubated with $10^{-8}$M diptheria toxin alone, $10^{-8}$M CRM107 alone or with the anti-transferrin receptor/anti-diphtheria toxin hybrid (7D3/D3E1) plus CRM107 at $10^{-8}$M was then measured.

FIG. 5 shows that both native toxin and the CRM107 hybrid combination gave identical kinetics profiles which were characterized by a 30–40 minute lag period followed by a rapid inactivation phase with $t_{1/2}=24$ minutes and $t_{1/2}=26$ minutes respectively. Unbound CRM107 alone at $10^{-8}$M had no effect on the ability of the cells to synthesize protein. The fact that hybrid-delivered CRM107 killed cells as fast as native diphtheria toxin suggests that its release from the antibody combining site was unimpeded and that there was no interruption of the normal course of events required for its lethal action.

Figure 6:
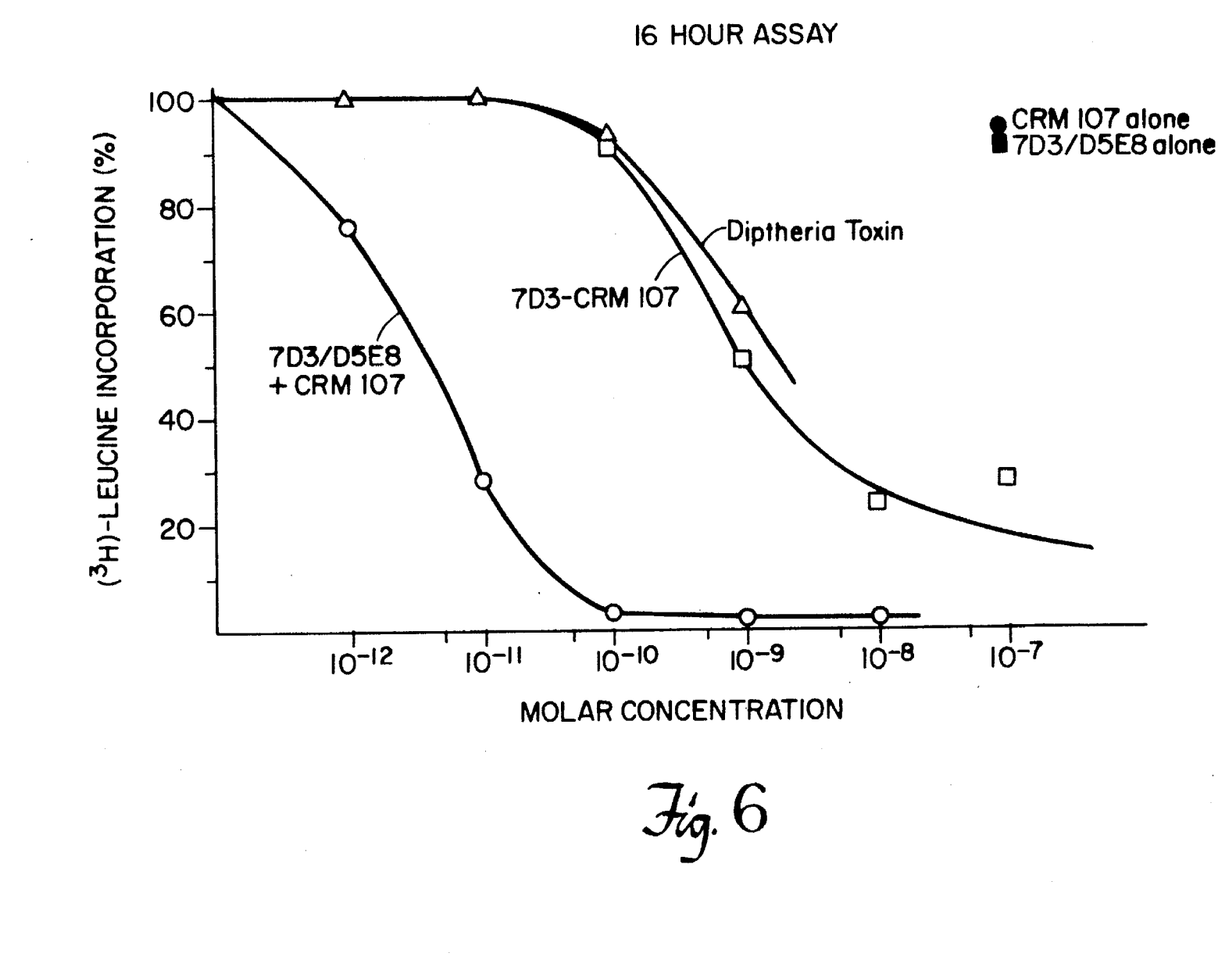
FIG. 6 is a graph plotting the toxicity dose-response curve for hybrids and conjugates incubated for 16 hrs. with transferrin receptor positive CEM cells.

Finally, a covalently-coupled anti-transferrin receptor-CRM107 conjugate (7D3-CRM107) was constructed by standard disulfide-linkage methods and its cytotoxic effect compared with the effect produced by the 7D3/D5E8 hybrid plus CRM107. Transferrin receptor positive CEM cells were incubated for 16 hours at 37° C. with the designated concentrations of the 7D3/D5E8 hybrid plus $10^{-7}$M CRM107, the 7D3-CRM107 disulfide-linked covalent conjugate and native diphtheria toxin, CRM107 alone or 7D3/D5E8 hybrid alone. The cells were then pulse labeled with $^3$H-leucine for 30 minutes and the amount of incorporation into protein was compared with untreated control cells.

FIG. 6 shows the toxicity dose response curves of the hybrid, the conjugate and native diphtheria toxin. The conjugate, 7D3-CRM107 was cytotoxic to transferrin receptor positive cells, the kinetics of cell killing was much slower than that found for hybrid-delivered CRM107. CEM cells are not particularly sensitive to diphtheria toxin as reflected in the $ID_{50}=2\times10^{-9}$M obtained with native toxin. The transferrin-receptor directed 7D3-CRM107 conjugate was slightly more effective, giving an $ID_{50}=1\times10^{-9}$M. In contrast, hybrid-delivered CRM107 ($ID_{50}=4\times10^{-12}$M) was 250-fold more potent than the covalent conjugate, based upon the concentration of hybrid added. Neither the 7D3/D5E8 hybrid alone nor CRM107 alone had an effect upon the cells. These results indicate that covalent coupling can impede toxin action since the disulfide-linked 7D3-CRM107 conjugate was slower acting and less potent than the corresponding 7D3/D5E8 hybrid delivered CRM107.

Figure 7:
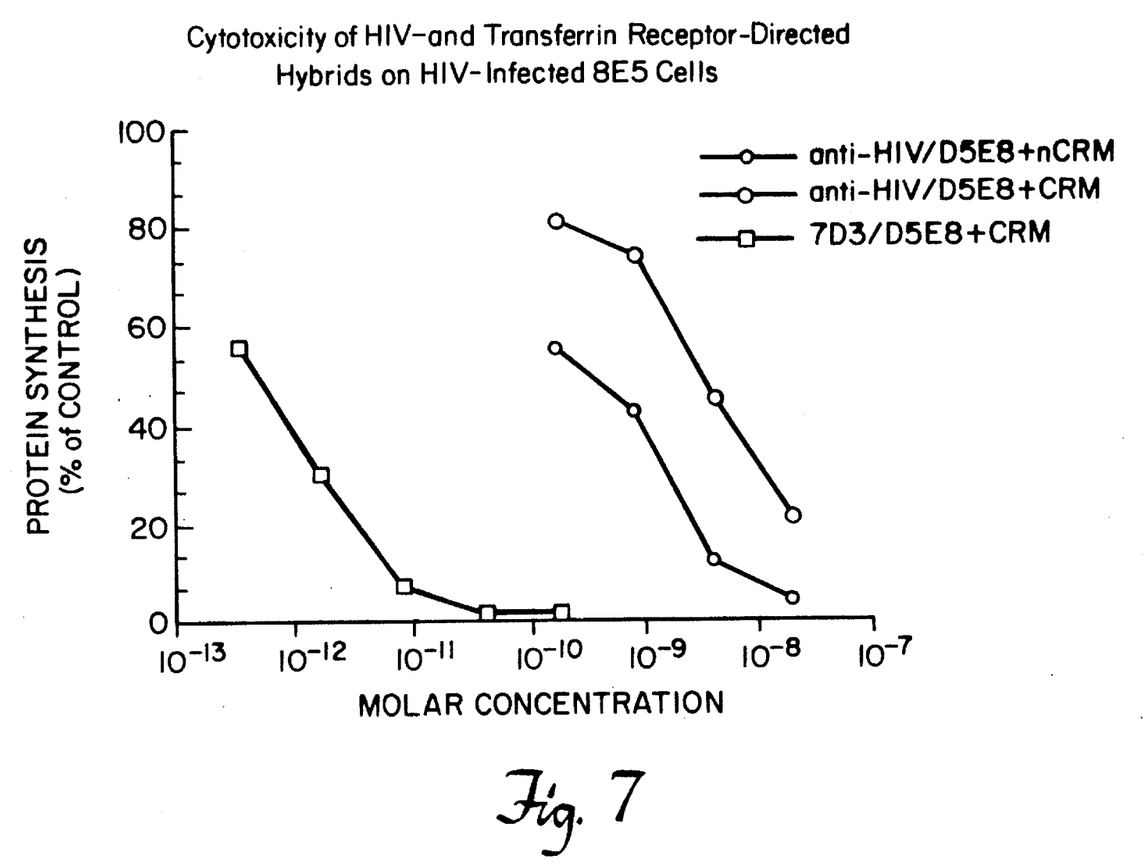
FIG. 7 is a graph plotting the toxicity dose-response curve for HIV and transferrin receptor directed hybrids on HIV-infected 8E5 cells.

FIG. 7 shows dose response curves for inhibition of protein synthesis in HIV-infected 8E5 cells after 16 hr exposure to CRM107 plus hybrids directed against either HIV or transferrin receptors on the cell membrane. The $ID_{50}$ for the anti-HIV/D5E8 hybrid plus CRM107 was $2\times10^{-9}$M but this reagent became 10-times more potent when nicked CRM107 (cleaved at a specific site using trypsin) was used ($ID_{50}=2\times10^{-10}$M). It is believed that proteolytic cleavage is a prerequisite for toxic activity and normally occurs at the cell surface or in subcellular compartments. This anti-HIV hybrid-mediated cytotoxicity was blocked by neutralizing intracellular compartments with $NH_4Cl$ (Table V) and the uninfected control cell line was not affected by hybrid-delivered CRM107.

EQUIVALENTS

Those skilled in the art will know, or be able to ascertain using no more than routine experimentation, many equivalents to the specific embodiments of the invention as described herein. These and all other equivalents are intended to be encompassed by the following claims.

I claim:

1. A hybrid reagent for delivering diphtheria toxin or a cytotoxic mutant or fragment thereof to a cellular target within cells of a host, comprising:

a) a first portion which, upon in vivo administration to the host at a first pH, delivers and binds said hybrid reagent to the surface of said cells with the subsequent pinching off of the surface of said cells to form endosomes having a second and lower pH and containing said hybrid reagent whereby the hybrid reagent is transported to the interior of said cells by endocytosis, said first portion comprising anti-transferrin receptor monoclonal antibody or an antigen binding fragment thereof; and b) a second portion comprising an antibody or antigen binding fragment which binds said diphtheria toxin or a cytotoxic mutant or fragment thereof at said first pH and releases it at a second and lower pH within the endosomes, said antibody or antigen binding fragment comprising monoclonal antibody specific towards diphtheria toxin or a fragment thereof;

whereby said hybrid reagent, upon in vivo administration to said host with the antibody or antibody fragment bound to the diphtheria toxin or a cytotoxic mutant or fragment thereof will bind to the surface of said cells, will be endocytosed into said cells and will release the diphtheria toxin or a cytotoxic mutant or fragment thereof to the cellular target within said cells.

2. A hybrid reagent of claim 1 wherein said first pH comprises a pH in the range of from about 6.5 to about 7.5.

3. A hybrid reagent of claim 2 wherein said second and lower pH comprises a pH in the range of from about 4.5 to about 5.5.

4. A composition comprising a hybrid reagent of claim 1 and an acceptable carrier.

5. A hybrid reagent for delivering diphtheria toxin or a cytotoxic mutant or fragment thereof to a cellular target within cells comprising:

a) a first portion which delivers and binds said hybrid reagent to the surface of said cells with the subsequent pinching off of the surface of said cells to form endosomes having a second and lower pH and containing said hybrid reagent whereby the hybrid reagent is transported to the interior of said cells by endocytosis, said first portion comprising anti-transferrin receptor monoclonal antibody or an antigen binding fragment thereof; and b) a second portion comprising an antibody or antibody fragment which binds said diphtheria toxin or a cytotoxic mutant or fragment thereof at said first pH and releases it at a second and lower pH within the endosomes, said antibody or antigen binding fragment comprising monoclonal antibody specific towards diphtheria toxin or a fragment thereof;

whereby said hybrid reagent with the antibody or antibody fragment bound to the diphtheria toxin or a cytotoxic mutant or fragment thereof will bind to the surface of said cells, will be endocytosed into said cells and will release the diphtheria toxin or a cytotoxic mutant or fragment thereof to the cellular target within said cells.

6. A hybrid reagent of claim 5 wherein said first pH comprises a pH in the range of from about 6.5 to about 7.5 and the second and lower pH comprises a pH in the range of from about 4.5 to about 5.5.

* * * * *